United States Patent [19]

Masters et al.

[11] Patent Number: 5,601,803
[45] Date of Patent: Feb. 11, 1997

[54] SILICA ABRASIVE DENTIFRICE OF REDUCED STRINGLESS AND IMPROVED FLAVOR

[76] Inventors: James G. Masters, 9 Londonderry Dr., Flemington, N.J. 08822; Michael Prencipe, 39 Spruce St., Princeton Junction, N.J. 08550; Julie A. Burke, 301 Jarvis Pl., Somerset, N.J. 08873; Linda J. Vellekoop, Rt. 1 Box 364 Amwell Rd., Neshanic, N.J. 08853

[21] Appl. No.: 451,289

[22] Filed: May 26, 1995

[51] Int. Cl.$^6$ .............................. A61K 7/16; A61K 7/18
[52] U.S. Cl. .................................... 474/49; 514/781
[58] Field of Search .................... 424/49–58; 514/781

[56] References Cited

U.S. PATENT DOCUMENTS

| | | | |
|---|---|---|---|
| 3,689,637 | 9/1972 | Pader | 424/52 |
| 3,934,000 | 1/1976 | Barth | 424/49 |
| 4,022,881 | 5/1977 | Hawking | 424/52 |
| 4,427,681 | 1/1984 | Munshi | 424/260 |
| 4,485,089 | 11/1984 | Leipold | 424/49 |
| 4,565,692 | 1/1986 | Mulvey et al. | 424/57 |
| 4,584,189 | 4/1986 | Leipold | 424/54 |
| 4,744,987 | 5/1988 | Mehra et al. | 424/156 |
| 5,192,529 | 3/1993 | Garlick et al. | 424/49 |
| 5,366,742 | 11/1994 | Tuason et al. | 426/96 |
| 5,441,753 | 8/1995 | McGinley et al. | 426/96 |
| 5,462,761 | 10/1995 | McGinley et al. | 426/573 |

*Primary Examiner*—Shep K. Rose
*Attorney, Agent, or Firm*—Paul Shapiro

[57] ABSTRACT

There is disclosed a flavored silica abrasive dentifrice which delivers higher levels and intensity of flavor and exhibits less stringiness the dentifrice having incorporated therein a cellulose gel comprised of a coprocessed mixture of microcrystalline cellulose and a cellulose gum such as carboxymethylcellulose.

22 Claims, No Drawings

SILICA ABRASIVE DENTIFRICE OF REDUCED STRINGLESS AND IMPROVED FLAVOR

FIELD OF THE INVENTION

This invention relates to silica abrasive dentifrice compositions, especially to silica abrasive toothpastes and dental gels having improved physical properties and flavor.

THE PRIOR ART

A thickening agent is commonly employed in dentifrice compositions to prevent separation of ingredients in storage, promote dispersibility and retention in use as on a toothbrush. Such thickeners are generally hydrophilic colloids which disperse in aqueous media. The most widely used thickeners are cellulose gums because they are cheap and their quality can be closely controlled. Carboxymethylcellulose is a widely used gum thickener in silica abrasive dentifrices but such dentifrices often exhibit excessive "stringiness" when extruded from a tube. Thus it has been found that the use of cellulose gums in the preparation of silica abrasive toothpastes or gels results in products that form a stringy tail which is attached to the end segment of the toothpaste portion extruded from a tube. If an excessive amount of tail forms, the dentifrice is characterized as having too much stringiness. Consumers view stringiness as aesthetically unpleasing. Consumers have come to expect a sharp-breaking paste such as provided by conventional high abrasive dentifrices. Further, the tail can unintentionally get onto the threads of the cap, neck and other portions of the tube creating an unappealing messy appearance to the product.

In addition to the stringiness problem, silica abrasive dentifrices have been found, for a given quantity of flavorant, to exhibit poor quality and distorted flavor profiles when compared to other abrasive dentifrices as for example, dicalcium phosphate abrasive toothpastes. The flavor distortion is believed to be caused by the absorption of some of the flavor components onto the silica particle surface which then distorts the flavor profile.

SUMMARY OF THE INVENTION

The present invention relates to a silica abrasive dentifrice which exhibits reduced stringiness and improved flavor quality which dentifrice is comprised of a silica dental abrasive, a humectant, water, flavor and a cellulose gel formed from a co-processed mixture of microcrystalline cellulose and a cellulose gum.

DESCRIPTION OF THE PREFERRED EMBODIMENTS

The dentifrice compositions of the present invention contain from about 15 to about 30% by weight and preferably about 18 to about 24% by weight of a silica abrasive. The silica abrasive used herein generally has an average particle size ranging between about 0.1 to 30 microns, preferably 5 to about 15 microns. Silica abrasive materials preferred in the practice of the present invention are those marketed by the J. M. Huber Corporation under the tradename "Zeodent" particularly the silica carrying the designation Zeodent 115.

The cellulose gel used as a thickener in the practice of the present invention is a cellulose gel formed from a dried, spray dried or bulk dried, co-processed, mixture of a microcrystalline cellulose and a cellulose gum such as carboxymethylcellulose, xanthan gum or sodium alginate.

An example of such cellulose gels are those sold by the FMC Corporation under the tradename Avicel. These cellulose gels, useful in the practice of the present invention, generally contain about 80 to about 90% by weight microcrystalline cellulose and about 10 to about 20% by weight cellulose gum. The particle size range of the gel is from submicron, that is, less than 0.2 micron to about 100 microns, and preferably about 0.2 to about 20 microns. A cellulose gel preferred for use in the practice of the present invention is Avicel RC-591-F which is a spray dried cellulose gel having the following composition and properties:

| | |
|---|---|
| % Microcrystalline Cellulose | 88 |
| % Colloidal (0.2 micron) | 70 |
| % carboxymethyl cellulose | 12 |
| Initial Viscosity* | 39–175 at 1.2% |
| Set Up Viscosity** | 1250 cps at 1.2% |

*Initial Viscosity: 120 secs. using a Brookfield ® RVT Viscometer #1 spindle at 20 rpms.
**Set-up Viscosity: 24 hours using a Brookfield ® RVT Viscometer #3 spindle at 20 rpms.

The cellulose gel is present in the dentifrice compositions of the present invention at a concentration of about 0.1 to about 1.0% by weight and preferably about 0.3 to about 0.5% by weight.

The vehicle used in the dentifrice compositions of this invention generally comprises about 6 to about 60% by weight of water and about 20 to about 70% by weight of humectant. The humectant content preferably ranges from about 40 to about 60% on a pure basis and the water content preferably ranges from about 10 to about 40%, and most preferably about 12 to about 20% by weight.

Humectants suitable for use in these dentifrice compositions include, for example, sorbitol (usually in the form of a 70% aqueous solution), glycerine, propylene glycol, xylitol, and/or polyethylene glycol (e.g. polyethylene glycol 400–600), especially mixtures of glycerine, sorbitol and polyethylene glycol.

In the dentifrice preparations of the present invention a fluoride ion releasing compound in an amount which releases about 25 to about 5,000 ppm of fluoride ion and preferably about 800 to about 1,500 ppm of fluoride ion is incorporated in the dentifrice. Fluoride compounds useful in the practice of the present invention include alkali metal fluorides such as sodium fluoride and stannous fluoride and sodium monofluorophosphate.

It will be understood that gum thickeners may be included in the dentifrice compositions of the present invention. Examples of such gum thickeners include xanthan gum, hydroxyethylcellulose and water-soluble salts of cellulose ethers such as carboxymethylcellulose and hydroxyethyl cellulose. Natural gums such as carrageenan (Irish moss, Viscarin), gum karaya, gum arabic, and gum tragacanth can also be used. Also useful are water soluble, hydrophilic colloidal carboxyvinyl polymers such as those available from the B. F. Goodrich Company under the trademark Carbopol 940P, 971P. Gum thickeners are included in the dentifrice compositions of the present invention at a concentration of about 0.25 to about 2.5% by weight and preferably about 1.0 to about 1.5% by weight.

Surfactants may be included in the dentifrice compositions of the present invention at a concentration of about 0.8 to 2.5% by weight and preferably about 1.0 to about 1.5% by weight. Examples of suitable surfactants include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkylaryl sulfonates such as sodium dodecyl benzene sulfonate higher alkyl sulfoacetates such as sodium lauryl sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbon atoms in the fatty acid, alkyl or acyl radicals, and the like.

Examples of suitable flavoring constituents useful in the practice of the present invention are flavoring oils, e.g. oil of spearmint, peppermint, wintergreen, sassafras, clove, sage, eucalyptus, marjoram, cinnamon, lemon, and orange, and methyl salicylate. The flavor oil is incorporated in the dentifrice composition of the present invention of a concentration of about 0.1 to 2.0% by weight and preferably about 0.5 to about 1.5% by weight.

Sweetening agents may be used in the preparation of the dentifrice compositions of the present invention. Suitable sweetening agents include sucrose, lactose, maltose, sorbitol, xylitol, sodium cyclamate, perillartine, aspartyl phenyl alanine, methyl ester, saccharine and the like. The sweetening agent comprises from about 0.1% to about 2% by weight of the dentifrice composition.

Pyrophosphate salts having anti-tartar efficacy such as a dialkali or tetra-alkali metal pyrophosphate salts such as $Na_4P_2O_7$, $K_4P_2O_7$, $Na_2K_2P_2O_7$, $Na_2H_2P_2O_7$, and $K_2H_2P_2O_7$, long chain polyphosphates such as sodium hexametaphosphate and cyclic phosphates such as sodium trimetaphosphate are incorporated in the dentifrice compositions of the present invention preferably at a concentration of about 0.5 to about 8.0% by weight and preferably about 1.5 to about 3% by weight.

Antibacterial agents may also be included in the oral compositions of the present invention. Especially useful are non-cationic antibacterial agents which are based on phenolic and bisphenolic compounds, halogenated diphenyl ether, benzoate esters and carbanilides. Examples of such compounds are 4-chlorophenol, 2,2'-trichloro-2-hydroxydiphenyl ether (Triclosan), esters of p-hydroxybenzoic acid, especially methyl, ethyl, propyl, butyl and benzyl esters, 3,4, 4'-trichlorocarbanalide and 3,3'4-trichlorocarbanilide. Triclosan in amounts ranging from 0.03% to 1% is preferred for use in the compositions of the present invention. Nonionic antimicrobial agents such as sesquiterpene alcohols such as merolidol and bisabolol are also useful in the present invention.

Tooth whitening agents may also be included in the oral compositions of the present invention. Especially useful are oxidizing agents such as calcium peroxide, hydrogen peroxide, urea peroxide, peracetic acid, sodium percarbonate. The amount of active oxygen in such oral compositions can vary from 0.1% to 5% by weight and preferably about 0.5% to about 2% by weight.

The dentifrice composition of the present invention may be prepared by mixing the ingredients wherein a first premix is prepared by dispersing a cellulose gel with a portion of the humectant and water. A second premix is prepared by mixing water with a fluoride compound such as sodium fluoride or sodium monofluorophosphate, and a sweetener such as saccharin are then added and mixed. A gel premix is prepared by dispersing a gum thickener and antitartar salt in a second portion of the humectant. After dispersion of the gel premix ingredients, the gel premix is combined with the second premix ingredients, to which is added a silica polishing agent such as Zeodent 115, a surfactant, flavor, and pigment. Other optional ingredients may then be added to the combined premixes. The combined second and gel premixes and first premix are added-sequentially to a suitable high speed mixer. These ingredients are then mixed under vacuum for about 15–30 minutes. The resulting gel or paste is then tubed.

The following examples are further illustrative of the present invention, but it is understood that the invention is not limited thereto. All amounts and proportions referred to herein and in the appended claims are by weight unless otherwise indicated.

EXAMPLE I

A toothpaste composition of the present invention containing a cellulose gel having a composition designated "A" was prepared in accordance with the practice of the present invention. A second comparative toothpaste composition designated "B" was prepared in which the cellulose gel was not included in the composition. The ingredients of compositions A and B are listed below:

| Ingredient | Composition Wt % | |
| --- | --- | --- |
| | A | B |
| Sorbitol | 46.307 | 34.557 |
| Glycerine | 10.000 | 22.00 |
| Polyethylene glycol | 3.00 | 3.00 |
| Carboxymethyl cellulose | 0.45 | 0.50 |
| Avicel RC591-F | 0.30 | — |
| Tetrasodium pyrophosphate | 0.50 | 0.50 |
| $TiO_2$ | 0.30 | 0.30 |
| Saccharin | 0.25 | 0.25 |
| NaF | 0.243 | 0.243 |
| Deionized Water | 12.00 | 12.00 |
| Zeodent 115 | 22.00 | 22.00 |
| Sylox 15* | 2.50 | 2.50 |
| Flavor** | 0.95 | 0.95 |
| Sodium lauryl sulfate | 1.20 | 1.20 |

*Silica thickener available from W. R. Grace
**Spearmint/peppermint mixture.

Composition A was prepared by mixing 15% sorbitol together with Avicel RC591-F until dispersed followed by the addition of 3% by weight water to prepare a first premix. A second premix was prepared by mixing sodium fluoride and saccaharin with water until dissolved. A gel premix was prepared by mixing the glycerin, carboxymethylcellulose, tetrasodium pyrophosphate and $TiO_2$ ingredients with the remainder of the sorbitol. The second premix and gel premix were then combined and transferred to a DOPP mixer followed by the first premix. Zeodent 115, NaF, flavor and sodium lauryl sulfate were added to the mixture, and the ingredients mixed under vacuum for about 15 minutes to obtain a homogeneous paste.

Composition B was prepared in a similar manner except Avicel RC 591F was not used in its preparation.

To assess the flavor release properties of compositions A and B, test specimens were prepared which were composed of an equal part mixture of undiluted toothpaste composition, toothpaste composition diluted 1:1 with water and toothpaste composition diluted 3:1 with water (ratios are weight ratios).

The flavor intensity of toothpaste compositions A and B was determined using a gas chromatograph. In this determination of flavor intensity, 5 milliliters (ml) of the toothpaste specimen is placed into a 22 ml vial and equibrated at 60° C. for an hour. The vapors eluted into the headspace of the vial are collected by a syringe and injected into the inlet of the gas chromatograph. The various components of the flavor oils retained on the gas chromatograph column elute out of the column at different retention times. Retention times of the eluted vapor on the gas chromatograph column are used to identify the different flavor components. The intensity of the flavor component is quantified by the area under the peak associated with the particular flavor component. The peak intensity is a measure of the amount of flavor released from the dentifrice; the higher the area under the peak the greater is the flavor intensity. The intensity results are recorded in Table I below.

For purposes of further comparison, a commercial silica abrasive gel dentifrice designated Composition C was also evaluated for flavor intensity. These comparative results are also recorded in Table I below.

TABLE I

Total Flavor Release From Mixed Dentifrices
Area under Peak × $10^6$

| Composition | Time-Weeks | | |
|---|---|---|---|
| | Initial | 6 | 16 |
| A | 27.2 | 26.9 | 25.9 |
| B | 25.8 | 24.9 | 24.0 |
| C | 26.2 | 26.0 | 23.8 |

The results recorded in Table I show that Composition A, which contains Avicel, yields higher flavor release than Composition B in which Avicel is absent as well as Composition C, the commercial silica abrasive gel dentifrice,

EXAMPLE II

To assess the stringiness of compositions A and B, toothpaste samples were sandwiched between two parallel stainless steel plates and an electrical current of 0.1–100 milliamperes was passed between the plates. The toothpaste sample served as a conducting medium for the current. The plates were then slowly drawn apart, and a string of paste was formed between the separating plates. Current flow stopped when the string of toothpaste was broken. The distance between the plates at string break point was measured, and this distance was a measure of the stringiness of the toothpaste sample. Stringiness was then quantified numerically by a "String Value" determined from a graph of the current as a function of time. The lower the String Value the less stringy and messy and the more consumer acceptable is the product.

The String Value of compositions A, B as well as composition C a commercial silica abrasive gel are recorded in Table II below:

TABLE II

| Composition | String Value |
|---|---|
| A | 5.1 |
| B | 10.0 |
| C | 14.1 |

The String Values recorded in Table II indicate that the dentifrice composition of the present invention, Composition A, has a String Value which is substantially less than comparative dentifrice Composition B in which a cellulose gel ingredient is absent as well as a commercial silica abrasive toothpaste (Composition C).

What is claimed is:

1. A dentifrice composition which exhibits enhanced flavor intensity and reduced stringiness, the dentifrice being comprised of a silica abrasive, water, humectant, flavor, thickener and a cellulose gel comprised of a coprocessed mixture of a microcrystalline cellulose and a cellulose gum.

2. The dentifrice composition of claim 1 wherein the cellulose gel contains about 80 to about 90% by weight of microcrystalline cellulose and about 10 to about 20% by weight of the cellulose gum.

3. The dentifrice composition of claim 1 wherein the cellulose gum is carboxymethylcellulose.

4. The dentifrice composition of claim 1 wherein the cellulose gel is present in the dentifrice at a concentration of about 0.1 to about 1.0% by weight.

5. The dentifrice composition of claim 1 wherein the flavor is present in the dentifrice at a concentration of about 0.1 to about 2% by weight.

6. The dentifrice composition of claim 1 wherein the silica abrasive is present in the dentifrice at a concentration of about 15 to about 30% by weight.

7. The dentifrice composition of claim 1 wherein water is present in the composition at a concentration of about 6 to about 60% by weight.

8. The dentifrice composition of claim 1 wherein the humectant is present in the composition at a concentration of about 20 to about 70% by weight.

9. The dentifrice composition of claim 1 wherein the thickener is present in the composition at a concentration of about 0.10 to about 2.5% by weight.

10. The dentifrice composition of claim 9 wherein the thickener is carboxymethyl cellulose.

11. A method for enhancing the flavor intensity and reducing the stringiness of silica abrasive dentifrices which comprises incorporating in the dentifrice containing a silica abrasive, water, humectant, flavor and thickener, a cellulose gel comprised of a coprocessed mixture of microcrystalline cellulose and a cellulose gum.

12. The method of claim 11 wherein the cellulose gel contains about 80 to about 90% by weight of the microcrystalline cellulose and about 10 to about 20% by weight of the cellulose gum.

13. The method of claim 11 wherein the cellulose gum is carboxymethylcellulose.

14. The method of claim 11 wherein the cellulose gel is present in the dentirice at a concentration of about 0.1 to about 1.0% by weight.

15. The method of claim 11 wherein the flavor is present in the dentifrice at a concentration of about 0.1 to about 2% by weight.

16. The method of claim 11 wherein the silica abrasive is present in the dentifrice at a concentration of about 15 to about 30% by weight.

17. The method of claim 11 wherein water is present in the composition at a concentration of about 6 to about 60% by weight.

18. The method of claim 11 wherein the humectant is present in the composition at a concentration of about 20 to about 70% by weight.

19. The method of claim 11 wherein the thickener is present in the composition at a concentration of about 0.25 to about 2.5% by weight.

20. The method of claim 19 wherein the thickener is carboxymethyl cellulose.

21. The composition of claim 1 wherein the cellulose gel is formed from a dried, spray dried or bulk dried, co-processed mixture of a microcrystalline cellulose and carboxymethyl cellulose.

22. The method of claim 11 wherein the cellulose gel is formed from a dried, spray dried or bulk dried, co-processed mixture of a microcrystalline cellulose and carboxymethyl cellulose.

* * * * *